US011160791B2

(12) United States Patent
Kolluru et al.

(10) Patent No.: US 11,160,791 B2
(45) Date of Patent: Nov. 2, 2021

(54) DEXMEDETOMIDINE INJECTION PREMIX FORMULATION IN READY TO USE (RTU) BAGS

(71) Applicant: Medefil, Inc., Glendale Heights, IL (US)

(72) Inventors: Lakshmi Prasanna Kolluru, Glendale Heights, IL (US); Zhiwen Guan, Glendale Heights, IL (US); Sunil Potdar, Glendale Heights, IL (US); Ravinder Malhotra, Glendale Heights, IL (US); Pradeep Aggarwal, Glendale Heights, IL (US)

(73) Assignee: Medefil, Inc., Glendale Heights, IL (US)

( * ) Notice: Subject to any disclaimer, the term of this patent is extended or adjusted under 35 U.S.C. 154(b) by 41 days.

(21) Appl. No.: 16/668,405

(22) Filed: Oct. 30, 2019

(65) Prior Publication Data

US 2020/0138788 A1    May 7, 2020

Related U.S. Application Data

(60) Provisional application No. 62/754,142, filed on Nov. 1, 2018.

(51) Int. Cl.
| | | |
|---|---|---|
| *A61K 31/4174* | (2006.01) | |
| *A61K 9/00* | (2006.01) | |
| *A61K 47/02* | (2006.01) | |
| *A61K 9/08* | (2006.01) | |

(52) U.S. Cl.
CPC ........ *A61K 31/4174* (2013.01); *A61K 9/0019* (2013.01); *A61K 9/08* (2013.01); *A61K 47/02* (2013.01)

(58) Field of Classification Search
CPC .................................................. A61K 31/4174
USPC ....................................................... 514/396
See application file for complete search history.

(56) References Cited

U.S. PATENT DOCUMENTS

| | | | |
|---|---|---|---|
| 4,407,957 | A | 10/1983 | Lim |
| 4,544,664 | A | 10/1985 | Karjalainen et al. |
| 4,670,455 | A | 6/1987 | Virtanen et al. |
| 4,910,214 | A | 3/1990 | Karjalainen et al. |
| 5,091,402 | A | 2/1992 | Kalso et al. |
| 5,124,157 | A | 6/1992 | Colley et al. |
| 5,217,718 | A | 6/1993 | Colley et al. |
| 5,304,569 | A | 4/1994 | Lammintausta |
| 5,344,840 | A | 9/1994 | Maze et al. |
| 5,520,639 | A | 5/1996 | Peterson et al. |
| 5,654,007 | A | 8/1997 | Johnson et al. |
| 5,704,911 | A | 1/1998 | Parsons |
| 5,712,301 | A | 1/1998 | Jaatinen et al. |
| 5,780,014 | A | 7/1998 | Eljamal et al. |
| 5,798,113 | A | 8/1998 | Dionne et al. |
| 5,814,607 | A | 9/1998 | Patton |
| 5,846,233 | A | 12/1998 | Lilley et al. |
| 6,716,867 | B1 | 4/2004 | Aantaa et al. |
| 8,242,158 | B1 | 8/2012 | Roychowdhury et al. |
| 8,338,470 | B1 | 12/2012 | Roychowdhury et al. |
| 8,436,033 | B1 | 5/2013 | Roychowdhury et al. |
| 8,648,106 | B2 | 2/2014 | Roychowdhury et al. |
| 9,320,712 | B2 * | 4/2016 | Roychowdhury ..... A61K 47/02 |
| 9,649,296 | B1 | 5/2017 | Pizza |
| 10,478,453 | B1 | 11/2019 | Maloney et al. |
| 10,583,155 | B1 | 3/2020 | Maloney et al. |

OTHER PUBLICATIONS

FDA, (2003) ICH Guidelines on Stability Testing of New Drugs and Products.*

* cited by examiner

*Primary Examiner* — Taofiq A Solola
(74) *Attorney, Agent, or Firm* — Taft Stettinius & Hollister LLP; Joseph M. Bennett-Paris

(57) ABSTRACT

The application provides pharmaceutical compositions comprising dexmedetomidine or a pharmaceutically acceptable salt thereof and sodium chloride, wherein the composition is disposed within a plastic container as a ready to use premixture. The application also provides a premixed, ready to use sterile dexmedetomidine solution comprising dexmedetomidine and sodium chloride, wherein the solution is provided within a plastic container. Also provided are methods of providing dexmedetomidine to a subject in need of such, wherein the composition is disposed within a sealed plastic container.

20 Claims, 1 Drawing Sheet

Representative Images of Dexmedetomidine Injection, 4μg/mL in a) Glass Vials and b) Ready to Use Bags
a)
b)

DEXMEDETOMIDINE INJECTION PREMIX FORMULATION IN READY TO USE (RTU) BAGS

FIELD OF THE INVENTION

The present invention relates to ready to use dexmedetomidine solutions disposed in a plastic container and methods of providing such solutions to a subject.

BACKGROUND OF THE INVENTION

Racemic 4-[1-(2,3-dimethylphenyl)ethyl]-1H-imidazole which is known under the name medetomidine, is a selective and potent $\alpha_2$-adrenoceptor agonist. Medetomidine has been used as an anti-hypertensive agent and as a sedative-analgesic agent. It has further been observed that this compound also possesses anxiolytic effects and can therefore be used in the treatment of general anxiety, panic disorder and various types of withdrawal symptoms.

The d-enantiomer of medetomidine, the generic name of which is dexmedetomidine, is described in U.S. Pat. No. 4,910,214 as an $\alpha_2$-adrenoceptor agonist for general sedation/analgesia and the treatment of hypertension or anxiety. U.S. Pat. Nos. 5,344,840 and 5,091,402 discuss dexmedetomidine in perioperative and epidural use, respectively. For example, when used in perioperative care, dexmedetomidine can reduce the amount of anesthetic necessary to anesthetize a patient. Additionally, U.S. Pat. No. 5,304,569 discusses the use of dexmedetomidine in treating glaucoma, and U.S. Pat. No. 5,712,301 discusses the use of dexmedetomidine for preventing neurodegeneration caused by ethanol consumption. Furthermore, U.S. Pat. No. 6,716,867 discloses methods of sedating a patient while in an intensive care unit by administering dexmedetomidine, or a pharmaceutically acceptable salt thereof, to the patient.

Dexmedetomidine can be administered to a subject in a variety of ways. For example, U.S. Pat. Nos. 4,544,664 and 4,910,214 disclose the administration of dexmedetomidine via parenteral, intravenous and oral routes. U.S. Pat. No. 4,670,455 describes intramuscular and intravenous administration, while U.S. Pat. Nos. 5,124,157 and 5,217,718 describe a method and device for administering dexmedetomidine through the skin. Additionally, U.S. Pat. No. 5,712,301 states that dexmedetomidine can be administered transmucosally.

Ready to use liquid pharmaceutical compositions comprising dexmedetomidine or a pharmaceutically acceptable salt thereof are described in U.S. Pat. Nos. 8,242,158; 8,648,106; 8,436,033; 8,338,470; and 8,242,158. The liquid pharmaceutical compositions comprising dexmedetomidine are packaged in glass containers because of the tendency of dexmedetomidine to be either adsorbed or absorbed by the plastic materials. The patents disclose loss of up to 20% of the dexmedetomidine from the liquid composition. The patents suggest the loss of dexmedetomidine can be reduced by including a buffer system in the formulation but even with a buffer, the patents indicated drug loss on the order of 10%. Additionally, the patents indicated all dexmedetomidine solutions stored in plastic containers contained more impurities than dexmedetomidine solutions stored in the glass containers tested therein.

Premixed, ready to use sterile dexmedetomidine solutions comprising dexmedetomidine and dextrose packaged in a plastic container substantially free of di-2-ethylhexyl phthalate (DEHP) are taught in U.S. Pat. No. 9,649,296. The patent teaches ionic salts such as sodium chloride results in substantial adsorption and/or absorption of the dexmedetomidine by plastic containers. When sodium chloride is used in dexmedetomidine solutions, U.S. Pat. No. 9,649,296 teaches a dexmedetomidine loss of at least 10%, even with buffers present.

SUMMARY OF THE INVENTION

The present application provides compositions of ready to use pharmaceutical compositions which can be terminally sterilized by moist heat sterilization and sterile solutions comprising dexmedetomidine stored in plastic containers and methods of providing dexmedetomidine to a subject wherein the dexmedetomidine solution is disposed within a sealed plastic container. The pharmaceutical compositions and sterile solutions provided by the present application are isotonic solutions comprising dexmedetomidine and sodium chloride.

In an embodiment the application provides a ready to use liquid pharmaceutical composition for parenteral administration to a subject, comprising dexmedetomidine or a pharmaceutically acceptable salt thereof and sodium chloride in an aqueous solution, wherein the liquid pharmaceutical composition is disposed within a sealed plastic container and wherein when the liquid pharmaceutical composition is stored in the plastic container for at least six months at 40° C.±2° C./NMT 25% RH, the liquid pharmaceutical composition exhibits no more than a 5% decrease in the concentration of dexmedetomidine. In various aspects, the plastic container may be a rigid plastic container, a bag, sack, tube, ampule, vial or syringe. In an aspect, the dexmedetomidine or pharmaceutically acceptable salt thereof in the liquid pharmaceutical composition is at a concentration of about 0.005 to about 100 µg/ml. In an aspect, the dexmedetomidine or pharmaceutically acceptable salt thereof in the liquid pharmaceutical composition is at a concentration of about 0.5 to about 10 µg/ml. In an aspect, the sodium chloride in the liquid pharmaceutical composition is at a concentration of about 1 to about 20 mg/ml. In an aspect, the sodium chloride in the liquid pharmaceutical composition is at a concentration of about 7 to 12 mg/ml.

In various aspects, the ready to use liquid pharmaceutical composition when stored in a plastic container for at least three months at 40° C.±2° C./NMT 25% RH exhibits no more than a 1% decrease in the concentration of dexmedetomidine. In an aspect, the ready to use liquid pharmaceutical composition when stored in the plastic container for at least six months exhibits no more than a 2% decrease in the concentration of dexmedetomidine. In various aspects, the liquid pharmaceutical composition is formulated as a total volume selected from the group consisting of 2 ml, 20 ml, 50 ml and 100 ml.

In an embodiment the application provides a premixed, ready to use sterile dexmedetomidine solution consisting of dexmedetomidine and sodium chloride in an aqueous solution packaged in a sealed plastic container, wherein the dexmedetomidine solution when stored in the plastic container at room temperature for at least six months exhibits no more than a 5% decrease in the dexmedetomidine concentration. In aspects of the application, the plastic container is a rigid plastic container, bag, sack, tube, ampule, vial or syringe. In an aspect of the solution, the dexmedetomidine or pharmaceutically acceptable salt thereof is at a concentration of about 0.005 to about 100 µg/ml. In an aspect, the sodium chloride may be at a concentration of between about 1 and about 20 mg/ml. In an aspect, the dexmedetomidine solution when stored in the plastic container for at least six months exhibits no more than a 5% decrease in the concentration of dexmedetomidine. In other aspects, the dexmedetomidine solution when stored in the plastic container for at least three months exhibits no more than a 2% decrease in the concentration of dexmedetomidine.

In an embodiment, the application provides methods of providing dexmedetomidine to a subject in need thereof. The method comprises administering to the subject an effective amount of a composition, wherein the composition comprises dexmedetomidine or a pharmaceutically acceptable salt thereof at a concentration of between about 0.005 to about 100 µg/ml, wherein the composition is a ready to use liquid pharmaceutical composition for parenteral administration to a subject disposed within a sealed plastic container. In aspects of the method, the sealed plastic container may be a rigid plastic container, a bag, sack, tube, ampule, vial or syringe. In aspects of the method, the composition is administered perioperatively. In aspects of the method, the composition is administered before or after surgery. In aspects of the method, the subject is non-ventilated or intubated. In aspects of the method, the composition is administered as an analgesic, an anxiolytic, an adjunct to anesthesia, a sedative or an anti-hypertensive agent.

BRIEF DESCRIPTION OF THE DRAWINGS

FIG. 1 provides representative images of a dexmedetomidine solution in glass vials (panel A) and a plastic container (panel B, ready to use bag).

DETAILED DESCRIPTION OF THE INVENTION

The present application is based in part on the discovery that dexmedetomidine prepared in a premixed formulation that does not require reconstitution or dilution prior to administration to a patient, remains stable and active after prolonged storage in plastic containers. Such premixed formulations therefore avoid the cost, inconvenience, and risk of contamination or overdose that can be associated with reconstituting or diluting a concentrated dexmedetomidine formulation prior to administration to a patient. Disposition of the pharmaceutical composition or packaging of the sterile dexmedetomidine solution within a plastic container reduces the risk of glass breakage and decreases the weight of the packaging, thus decreasing transportation costs.

In the specification and in the claims, the terms "including" and "comprising" are open-ended terms and should be interpreted to mean "including, but not limited to . . . " These terms encompass the more restrictive terms "consisting essentially of" and "consisting of".

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, the term "dexmedetomidine" refers to a substantially pure, optically active dextrorotary stereoisomer of medetomidine, as the free base or pharmaceutically acceptable salt. In one, non-limiting embodiment, dexmedetomidine has the formula (S)-4-[1-(2,3-dimethylphenyl,ethyl]-3H-imidazole. A pharmaceutically acceptable salt of dexmedetomidine may include, but is not limited to, inorganic acids such as hydrochloric acid, hydrobromic acid, sulfuric acid, nitric acid, phosphoric acid, and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. Preferably, the dexmedetomidine salt is dexmedetomidine-HCl.

The terms "premix" or "premixture" as used herein refer to a pharmaceutical composition that does not require reconstitution or dilution prior to administration to a patient. For example, in contrast to non-premixed formulations of dexmedetomidine, the premixed compositions provided herein are suitable for administration to a subject without dilution by, for example, a clinician, hospital personnel, caretaker, patient or any other individual.

In certain embodiments, the compositions of the present invention can be formulated as "ready to use" compositions which refer to premixed compositions that are suitable for administration to a patient without dilution. For example, in certain embodiments, the compositions of the present application are "ready to use" upon removing the compositions from a sealed container or vessel, upon piercing or puncturing the sealed container.

In certain embodiments, the compositions of the present invention can be formulated as a "single use dosage" which refers to a premixed composition that is disposed within a sealed container or vessel as one dose per container or vessel formulation.

A "subject" or "patient" is a human, a non-human mammal or a non-human animal. Although the animal subject may be human, the compounds and compositions of the invention have application in veterinary medicine as well, e.g., for the treatment of domesticated species such as canine, feline and various other pets; farm animal species such as bovine, equine, ovine, caprine, porcine, etc.; wild animals, e.g. in the wild or in a zoological garden; and avian species such as chickens, turkeys, quail, songbirds, etc.

The term "purified" as used herein refers to material that has been isolated under conditions that reduce or eliminate the presence of unrelated materials, i.e. contaminants, including native materials from which the material is obtained. As used herein, the term "substantially free" is used operationally, in the context of analytic testing of the material. Preferably, purified material substantially free of contaminants is at least 95% pure, more preferably at least 97% pure, yet more preferably at least 99% pure. Purity can be evaluated for example by chromatography or any other methods known in the art. In particular embodiments purified means that the level of contaminants is below a level acceptable to regulatory authorities for safe administration to a human or a non-human animal.

The term "pharmaceutically acceptable," when used in connection with the pharmaceutical compositions of the application, refers to molecular entities and compositions that are physiologically tolerable, and do not typically produce untoward reactions when administered to a human. Preferably as used herein, the term "pharmaceutically acceptable" means approved by a regulatory agency of the Federal or state government or listed in the U.S. Pharmacoepia or other generally recognized pharmacopeia for use in animals, and more particularly in humans. The term "carrier" refers to a diluent, excipient, dispersing agent or vehicle with which the composition is administered. Such pharmaceutical carriers can be sterile liquids, such as water and oils. For example water, aqueous solutions, saline solutions or aqueous glycerol solutions can be employed as carriers, particularly for injectable solutions. Suitable pharmaceutical carriers are described in, for example, "Remington's Pharmaceutical Sciences" by Philip P. Gerbino, $22^{nd}$ Edition). Aqueous solutions are those in which water is the solvent. The term "pharmaceutical composition" as used in accordance with the present application relates to compositions that can be formulated in any conventional manner using one or more pharmaceutically acceptable carriers or excipients.

The term "dosage" is intended to encompass a formulation expressed in terms of µg/kg/day, µg/kg/hr, mg/kg/day or mg/kg/hr. The dosage is the amount of an ingredient administered in accordance with a particular dosage regimen. A "dose" is an amount of an agent administered to a mammal in a unit volume or mass, e.g., an absolute unit dose expressed in mg or µg of the agent. The dose depends on the concentration of the agent in the formulation, e.g. in moles per liter (M), mass per volume (m/v) or mass per mass (m/m). The two terms are closely related, as a particular dosage results from the regimen of administration of a dose or doses of the formulation. The particular meaning in any case will be apparent from context.

The terms "therapeutically effective dose," "effective amount", and "therapeutically effective amount" refer to an amount sufficient to produce the desired effect. In the non-limiting embodiments, a "therapeutically effective dose" means an amount sufficient to reduce by at least about 15%, preferably by at least 50%, more preferably by at least 90% and most preferably prevent a clinically significant deficit in the activity, function and response of the host. Alternatively, a therapeutically effective amount is sufficient to cause an improvement in a clinically significant condition in the recipient. These parameters will depend on the severity of the condition being treated, other actions that are being implemented such as administration of other compounds, the weight, age and sex of the subject, and other criteria, which can be readily determined according to good medical practice by those of skill in the art.

In other non-limiting embodiments, a therapeutic response may be any response that a user (for example a clinician or other medical professional), will recognize as an effective response to the therapy. Thus, a therapeutic response will generally be an induction of a desired effect, such as, for example, sedation or analgesia.

The terms "about" or "approximately" as used herein mean within an acceptable error range for the particular value as determined by one of ordinary skill in the art, which will depend in part on how the value is measured or determined, i.e. the limitations of the measurement system. For example, "about" can mean within 3 or more than 3 standard deviations, per the practice in the art. Alternatively, particularly with respect to biological systems or processes, the term can mean within an order of magnitude, preferably within 5-fold and more preferably within 2-fold, of a value.

The compounds and compositions of the application may be formulated as pharmaceutical compositions by admixture with a pharmaceutically acceptable carrier or excipient. In certain non-limiting embodiments, the compounds or compositions are provided in a therapeutically effective amount to an animal such as a mammal, preferably a human, in need of treatment therewith for inducing a sedative, anxiolytic, analgesic or anesthetic effect.

In certain non-limiting embodiments, dexmedetomidine is formulated as a composition, wherein the dexmedetomidine is the only therapeutically active ingredient present in the composition. In another non-limiting embodiment, dexmedetomidine is formulated as a composition, wherein the dexmedetomidine is formulated in combination with at least one or more therapeutically active ingredient. In other non-limiting embodiments, the dexmedetomidine is administered to a subject in conjunction with at least one or more other therapeutically active ingredients. Such administration may be prior to, concomitant with or consecutive to the administration of the at least one other therapeutically active ingredient. The formulation is preferably suitable for parenteral administration, including but not limited to, intravenous, subcutaneous, intramuscular and intraperitoneal administration. However, formulations suitable for other routes of administration such as oral, intranasal, mucosal or transdermal are also contemplated.

The pharmaceutical formulations suitable for injectable use, such as, for example, intravenous, subcutaneous, intramuscular and intraperitoneal administration include sterile aqueous solutions or dispersions. In all cases, the form can be sterile and can be fluid to the extent that easy syringability exists. It can be stable under the conditions of manufacture and storage and can be preserved against the contaminating action of microorganisms such as bacteria and fungi. A composition or solution that "is stable" exhibits no more than a 5% decrease in the concentration of dexmedetomidine, or exhibits no more than a 4% decrease in the dexmedetomidine concentration, or exhibits no more than a 3% decrease in the dexmedetomidine concentration, or exhibits no more than a 2% decrease in the dexmedetomidine concentration, or exhibits no more than a 1% decrease in the dexmedetomidine concentration, or exhibits no more than a 0.5% decrease in the dexmedetomidine concentration at the indicated time span. Methods of testing stability under less than optimal conditions such as elevated temperature to predict longer term stability are known in the art. Accelerated stability conditions allow predictions of composition stability at durations at least as long as 24 months. The carrier can be a solvent or dispersion medium containing for example, water, saline, ethanol, polyol (for example glycerol, propylene glycol, polyethylene glycol and the like), suitable mixtures thereof and oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example parabens, chlorobutanol, phenol benzyl alcohol, sorbic acid and the like.

In many cases, it will be preferable to include an isotonic agent like sodium chloride. Prolonged absorption of the injectable compositions can be brought about by the use in the compositions of agents delaying absorption, for example aluminum monostearate and gelatin. Sterile solutions may be prepared by incorporating the dexmedetomidine in the required amounts in the appropriate solvent with the various other ingredients as required, followed by filter or terminal sterilization. Generally, dispersions are prepared by incorporating the various sterilized active ingredients in a sterile vehicle which contains the basic dispersion medium and the required other ingredients.

In various embodiments, the formulation may comprise a pharmaceutically acceptable excipient. As used herein, the term "stabilizer" refers to a compound optionally used in various embodiments to avoid the need for sulfite salts and increase storage life. Non-limiting examples may include anti-oxidants. Buffer systems for use in the present embodiments may include citrate, acetate, bicarbonate and phosphate buffers. The compositions may also include a non-ionic detergent.

The parenteral formulations of the present application may be sterilized. Non-limiting examples of sterilization techniques include filtration through a bacterial-retaining filter, terminal sterilization, incorporation of sterilizing agents, irradiation and heating.

The route of administration may be parenteral or oral, including intravenous, subcutaneous, intra-arterial, intraperitoneal, ophthalmic, intramuscular, rectal, vaginal, intraorbital, intracerebral, intradermal, intracisternal, intracapsular, intraspinal, epidural, intrapulmonary, intranasal, transmucosal, transdermal, via inhalation or buccal.

Administration of the above-described parenteral formulations may be by periodic injections of a bolus of the preparation or may be administered by intravenous or intraperitoneal administration from a reservoir which is external (e.g. intravenous bag) or internal (e.g. a bioerodable implant, a bioartificial or an organ). See e.g. U.S. Pat. Nos. 4,407,957 and 5,798,113 each incorporated herein by reference in their entirety. Intrapulmonary delivery methods and apparatus are described for example, in U.S. Pat. Nos. 5,654,007; 5,780,014, and 5,814,607, each incorporated herein by reference in their entireties. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation and transdermal patches. Needle-less injector devices are described in U.S. Pat. Nos. 5,879,327; 5,520,639; 5,846,233 and 5,704,911, the specifications of which are hereby incorporated by reference in their entireties. Any of the formulations described herein can be administered in these methods.

In yet another non-limiting embodiment, the therapeutic compound can be delivered in a controlled or sustained release system. For example, a compound or composition may be administered using intravenous infusion, an implantable osmotic pump, a transdermal patch, liposomes, or other modes of administration. In one embodiment, a pump may be used (see Sefton, 1987, CRC Crit. Ref. Biomed. Eng 14:201; Buchwald et al, 1980, Surgery 88:507, Saudek et al 1989, N. Eng. J. Med. 321:574). In another embodiment, polymeric materials can be used (see Langer and Wise eds., 1974, Medical Applications of Controlled Release, CRC Press: Boca Raton, Fla.; Smolen and Ball, eds. 1984, Controlled Drug Bioavailability, Drug Product Design and Performance, Wiley, N.Y.; Ranger and Peppas, 1983, J. Macromol. Sci. Rev. Macromol. Chem., 23:61; Levy et al 1985, Science 228:190; During et al, 1989, Ann. Neurol. 25:351; Howard et al, 1989 J. Neurosurg. 71:105). In yet another embodiment, a controlled release system can be placed in proximity of the therapeutic target, i.e. the brain, thus requiring only a fraction of the systemic dose (see, e.g., Goodson 1984, in Medical Applications of Controlled Release, vol. 2, pp. 115-138).

In certain non-limiting embodiments, the ready to use pharmaceutical composition comprises dexmedetomidine or a pharmaceutically acceptable salt thereof at a concentration of between about 0.005 µg/mL and about 100 µg/ml, or between about 0.005 µg/ml and about 50 µg/ml, or between 0.005 µg/ml and about 25 µg/ml, or between about 0.005 µg/ml and about 15 µg/ml, or between about 0.005 µg/ml and about 7 µg/ml, or between about 0.01 µg/ml and about 5 µg/ml, or between about 0.01 µg/ml and about 4 µg/ml, or between about 0.01 µg/ml and about 3 µg/ml, or between about 0.01 µg/ml and about 2 µg/ml, or between about 0.01 µg/ml and about 1 µg/ml, or between about 0.01 µg/ml and about 0.5 µg/ml, or between about 0.01 µg/ml and about 0.05 µg/ml, or between about 0.5 to about 10 µg/ml.

In certain non-limiting embodiments, the ready to use pharmaceutical composition comprises dexmedetomidine or a pharmaceutically acceptable salt thereof, at a concentration of between about 3.5 µg/ml, and about 4.5 µg/ml, or between about 3 µg/ml and about 5 µg/ml, or between about 2.5 µg/ml and about 5.5 µg/ml, or between about 2 µg/ml and about 6 µg/ml, or between about 1.5 µg/ml or about 6.5 µg/ml, or between about 1 µg/ml and about 7 µg/ml, or between about 0.5 µg/ml and about 10 µg/ml.

In certain non-limiting embodiments, the ready to use pharmaceutical composition comprises dexmedetomidine or a pharmaceutically acceptable salt thereof at a concentration of about 0.5 µg/ml, or about 1 µg/ml, or about 1.5 µg/ml, or about 2 µg/ml, or about 2.5 µg/ml, or about 3 µg/ml, or about 3.5 µg/ml, or about 4 µg/ml, or about 4.5 µg/ml, or about 5 µg/ml, or about 5.5 µg/ml, or about 6 µg/ml, or about 6.5 µg/ml, or about 7 µg/ml, or about 7.5 µg/ml, or about 8 µg/ml, or about 8.5 µg/ml, or about 9 µg/ml, or about 9.5 µg/ml, or about 10 µg/ml, or about 10.5 µg/ml, or about 11 µg/ml, or about 11.5 µg/ml, or about 12 µg/ml, or about 12.5 µg/ml, or about 13 µg/ml, or about 13.5 µg/ml, or about 14 µg/ml, or about 14.5 µg/ml, or about 15 µg/ml, or about 15.5 µg/ml, or about 16 µg/ml or about 16.5 µg/ml, or about 17 µg/ml, or about 17.5 µg/ml, or about 18 µg/ml, or about 18.5 µg/ml, or about 19 µg/ml, or about 19.5 µg/ml or about 20 µg/ml.

In certain non-limiting embodiments, the ready to use pharmaceutical composition comprises dexmedetomidine at a concentration of about 4 µg/ml.

In certain non-limiting embodiments, the ready to use pharmaceutical composition is formulated as a liquid.

In certain non-limiting embodiments, the ready to use sterile solution comprises dexmedetomidine at a concentration of between about 0.005 µg/mL and about 100 µg/ml, or between about 0.005 µg/ml and about 50 µg/ml, or between 0.005 µg/ml and about 25 µg/ml, or between about 0.005 µg/ml and about 15 µg/ml, or between about 0.005 µg/ml and about 7 µg/ml, or between about 0.01 µg/ml and about 5 µg/ml, or between about 0.01 µg/ml and about 4 µg/ml, or between about 0.01 µg/ml and about 3 µg/ml, or between about 0.01 µg/ml and about 2 µg/ml, or between about 0.01 µg/ml and about 1 µg/ml, or between about 0.01 µg/ml and about 0.5 µg/ml, or between about 0.01 µg/ml and about 0.05 µg/ml.

In certain non-limiting embodiments, the ready to use sterile solution comprises dexmedetomidine at a concentration of between about 3.5 µg/ml, and about 4.5 µg/ml, or between about 3 µg/ml and about 5 µg/ml, or between about 2.5 µg/ml and about 5.5 µg/ml, or between about 2 µg/ml and about 6 µg/ml, or between about 1.5 µg/ml or about 6.5 µg/ml, or between about 1 µg/ml and about 7 µg/ml, or between about 0.5 µg/ml and about 10 µg/ml.

In certain non-limiting embodiments, the ready to use sterile solution comprises dexmedetomidine at a concentration of about 0.5 µg/ml, or about 1 µg/ml, or about 1.5 µg/ml, or about 2 µg/ml, or about 2.5 µg/ml, or about 3 µg/ml, or about 3.5 µg/ml, or about 4 µg/ml, or about 4.5 µg/ml, or about 5 µg/ml, or about 5.5 µg/ml, or about 6 µg/ml, or about 6.5 µg/ml, or about 7 µg/ml, or about 7.5 µg/ml, or about 8 µg/ml, or about 8.5 µg/ml, or about 9 µg/ml, or about 9.5 µg/ml, or about 10 µg/ml, or about 10.5 µg/ml, or about 11 µg/ml, or about 11.5 µg/ml, or about 12 µg/ml, or about 12.5 µg/ml, or about 13 µg/ml, or about 13.5 µg/ml, or about 14 µg/ml, or about 14.5 µg/ml, or about 15 µg/ml, or about 15.5 µg/ml, or about 16 µg/ml or about 16.5 µg/ml, or about 17 µg/ml, or about 17.5 µg/ml, or about 18 µg/ml, or about 18.5 µg/ml, or about 19 µg/ml, or about 19.5 µg/ml or about 20 µg/ml.

In certain non-limiting embodiments, the ready to use sterile solution comprises dexmedetomidine at a concentration of about 4 µg/ml.

In certain non-limiting embodiments, the ready to use pharmaceutical composition or the ready to use sterile solution is formulated at a pH of between about 1 and about 10, or between about 1 and about 8, or between about 2 and about 7, or between about 3 and about 7. In other non-limiting embodiments, the ready to use solution is formulated at a pH of between about 4.5 and 7.0. In other non-limiting embodiments, the ready to use pharmaceutical composition or sterile solution comprises dexmedetomidine mixed or dissolved in a sodium chloride saline solution. The saline solution can comprise sodium chloride present at a concentration of between about 0.05 weight percent and about 10 weight percent, or between about 0.05 weight percent and about 9 weight percent, or between about 0.05 weight percent and about 5 weight percent, or between about 0.05 weight percent and about 3 weight percent, or between about 0.05 weight percent and about 2 weight percent, or between about 0.05 weight percent and about 1 weight percent. In one preferred, non-limiting embodiment of the composition or solution, the sodium chloride is present at a concentration of about 0.9 weight percent.

In certain embodiments the weight percent of the saline solution is a percent weight/weight of the ready to use composition or solution. In certain embodiments, the weight percent of the saline solution is a percent weight/volume of the ready to use composition or solution.

In certain non-limiting embodiments, the ready to use pharmaceutical composition or ready to use solution of the present application comprises dexmedetomidine or a pharmaceutically acceptable salt thereof at a concentration of between about 0.05 µg/ml and about 15 µg/ml, and sodium chloride at a concentration of between about 0.01 and about 2.0 weight percent. In other non-limiting examples, sodium chloride is at a concentration of between about 0.5 to about 20 mg/ml. In other non-limiting examples, sodium chloride is at a concentration of between about 7 to about 12 mg/ml. In other non-limiting embodiments, the ready to use dexmedetomidine composition of the present application comprises dexmedetomidine or a pharmaceutically acceptable salt thereof at a concentration of about 4 µg/ml and sodium chloride at a concentration of about 0.9 weight percent.

In one non-limiting example, the 0.9% NaCl solution is formulated by mixing 9.0 g NaCl/1000 ml of water. In certain embodiments, the ready to use compositions are formulated by adding 0.118 g dexmedetomidine HCl plus 9.0 g NaCl into the same 1000 ml of water. The solution can then be mixed with addition 0.9% NaCl solution to achieve a desired concentration of dexmedetomidine, for example 4 µg/ml.

In certain non-limiting embodiments, the ready to use pharmaceutical composition or dexmedetomidine solution is disposed in a sealed plastic container or vessel that can maintain the sterility of, or prevent the contamination of, a ready to use dexmedetomidine composition that is purified or substantially free of contaminants. In certain non-limiting embodiments, the container or vessel is a sealed plastic container or vessel. In certain non-limiting embodiments, the dexmedetomidine composition or solution is disposed or packaged in a container or vessel and is formulated as a premixture. In certain non-limiting embodiments, the ready to use composition or solution is disposed in a plastic container or vessel and is formulated as a single use dosage. In certain non-limiting embodiments, the ready to use dexmedetomidine composition is disposed in container or vessel and is formulated as a dosage for multiple uses.

In certain non-limiting embodiments, the plastic container or vessel includes but is not limited to a rigid plastic container, bag, sack, tube, ampule, vial or syringe, and flexible plastic containers. In non-limiting embodiments, the plastic container is made of copolymerized ethylene and vinyl acetate. In non-limiting embodiments, the plastic container is made of polypropylene. In non-limiting embodiments the bag is laminated with the inner most layer comprising copolymerized ethylene and vinyl acetate. In non-limiting embodiments, the plastic container comprises three to seven layers. The volume of the container is dependent on the desired volume of the ready to use composition or solution. The volume of the ready to use composition can be from 0.5 ml to 1.5 L, or from 1 ml to 200 ml, or from 1 ml to 100 ml, or from 2 ml to 50 ml, or from 5 ml to 20 ml, or from 2 ml to 20 ml, or from 2 ml to 10 ml. Larger or smaller volumes can be used depending on dosing requirements.

Plastic containers suitable for use in the compositions may include but are not limited to those available under the tradename Nexcel by Sealed Air, containers with an inner layer comprising a styrene-ethylene-butylene-styrene (SEBS) and an ethylene-propylene copolymer, containers made of CR3 elastomer copolyester ether, containers made of polyolefin, PVC, polypropylene, or containers substantially free of DEHP. Substantially free of DEHP means that the amount of DEHP present is insufficient to appreciably impact the amount of dexmedetomidine retained in the solution upon storage stability testing. That is, the amount of dexmedetomidine remains at or above 90% of the initial level.

In a non-limiting embodiment of the present application, provided are a flexible plastic container with modified ports and closure system suitable for storing dexmedetomidine formulations of the present invention which is subjected to product sterilization by steam sterilization or other sterilization means without altering the thermal properties of the film layers, ports and closure system as well as maintaining the integrity container. The primary polymeric materials may include, but are not limited to, polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer, Inerta® Polypropylene film from Technoflex and ABS. In addition to plastic bags, CZ resin containers, polypropylene and similar resins can be used as rigid containers and syringes. In an exemplary embodiment of the present application, the pharmaceutical composition is packaged within Inerta™ film bags from Technoflex.

The ports and the closure system preferably use commercially available polymers, elastomers, etc. In non-limiting embodiments of the present application, the administrative and additive ports can be made of an external coextruded layer consisting of synthetic thermoplastic rubber (Raumedic SRT320) ranging from about 20 to 30% based on an elastomer modified polypropylene. The internal coextruded layer (PE770) may be not more than 50% in composition of ethylene vinyl acetate (EVA) with minimal further additives. The tubing ports can be made of two-layer materials, which can withstand both terminal sterilization and co-solvent matrix. Furthermore, the twist-off compositions can be made of polypropylene Granuflex™4489 between 70-80% and Granuflex™4371 15-20%. Alternatively the port tube may be a bilayer tube comprising an outer layer of polypropylene and an inner layer of EVA and the twist off made of LDPE and PP. However, other stable polymers with low leachables and without physical deformation during heat sterilization may also be used for the ports and closure assemblies.

Commercially available flexible plastic containers including but not limited to bags such as Excel™ (Braun Co) comprising a three-layered ethylene-polypropylene bag having polyester elastomer outer layer, Visiv™ (Hospira), Nexcel™ (Sealed Air), Intervia™ (Baxter), including those with a non-DEHP fluid path, Technoflex polyolefin bags, bags, sacks, and tubes for pharmaceutical compositions or medical solutions are assembled of different plastic materials of different properties, thermal resistance and functionalities. They are typically designed and tested mostly for aqueous formulations admixtures, premixed or ready to use pharmaceutical products. In some embodiments, the plastic container is preferable a bag which can be manufactured with or without an overwrap.

It is recognized some co-solvents and drug compositions subjected to further heat sterilization may adversely affect plastic materials, sealing integrity and the solutions contained therein unless they are maintained at certain conditions. Thus the plastic container should be checked after sterilization for integrity before using it for formulation. In addition, in some embodiments it may be advisable to analyze the formulation after sterilization for the presence of substances leached from the container as a result of the sterilization cycle.

In other non-limiting embodiments, the application provides flexible plastic containers with modified ports and closure system suitable for storing dexmedetomidine formulations of the present application which are subjected to product sterilization by steam sterilization without altering the thermal properties of the film layers, ports and closure system as well as maintaining the integrity container. The primary polymeric materials which may be used include, but are not limited to, polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer, etc.

Sterilization may be accomplished by any of the conventional sterilization methods known in the art including, but not limited to, aseptic filling, irradiation and heat sterilization. Heat sterilization may be performed using steam, preferably wet steam to allow for the use of pressure as a means of temperature control. The time period for the sterilization must be long enough to meet the sterility requirements required of an injectable product. When steam is used the period may be from about 5 to about 60 minutes at temperatures of about 100° C. to 130° C., or from about 10 minutes to 60 minutes at temperatures of about 100° C. to 130° C., preferably at 120° C. to 125° C. for 15 to 60 minutes. In another embodiment the sterilization can be at 120° C. for about 5 to about 60 minutes.

In certain non-limiting embodiments, the ready to use dexmedetomidine solutions or pharmaceutical compositions may be stored as a liquid in an aliquot having a total volume between about 0.1 and 1500 ml, or between about 0.1 and 1000 ml, or between about 0.1 and 500 ml, or between about 0.1 and 250 ml, or between about 0.5 ml and 250 ml, or between about 0.5 ml and 100 ml, or between about 1 ml and 100 ml, or between about 1 and 90 ml, or between about 1 and 80 ml, or between about 1 and 70 ml, or between about 1 and 60 ml, or between about 1 and 50 ml, or between about 1 and 40 ml, or between about 1 and 30 ml, or between about 1 and 20 ml, or between about 1 and 10 ml, or between about 1 and 5 ml, or between about 1 and 2.5 ml.

In certain non-limiting embodiments, the ready to use dexmedetomidine compositions may be stored as a liquid in an aliquot having a total volume of about 2 ml. In certain non-limiting embodiments, the ready to use dexmedetomidine compositions may be stored as a liquid in an aliquot having a total volume of about 5 ml. In certain non-limiting embodiments, the ready to use dexmedetomidine compositions may be stored as a liquid in an aliquot having a total volume of about 10 ml. In certain non-limiting embodiments, the ready to use dexmedetomidine compositions may be stored as a liquid in an aliquot having a total volume of about 20 ml. In certain non-limiting embodiments, the ready to use dexmedetomidine compositions may be stored as a liquid in an aliquot having a total volume of about 50 ml. In certain non-limiting embodiments, the ready to use dexmedetomidine compositions may be stored as a liquid in an aliquot having a total volume of about 100 ml. In certain non-limiting embodiments, the ready to use dexmedetomidine compositions may be stored as a liquid in an aliquot having a total volume of about 250 ml. In certain non-limiting embodiments, the ready to use dexmedetomidine compositions may be stored as a liquid in an aliquot having a total volume of about 500 ml.

In certain non-limiting embodiment, the present application provides for perioperative treatment of a patient to reduce the response of the autonomic nervous system to stimuli during an operation by administering a dexmedetomidine composition of the application. In other non-limiting embodiments, the dexmedetomidine compositions may be administered as a sedative. In certain embodiments, the composition is administered peri-operatively to potentiate the effects of an anesthetic, wherein administration of the composition reduces the amount of anesthetic required to achieve a desired level of anesthesia. In certain embodiments, the dexmedetomidine compositions of the present invention can be administered as an anxiolytic analgesic premedication prior to the operation with or without administration of an amount of anesthetic effective to achieve a desired level of local or general anesthesia. In certain embodiments, the dexmedetomidine compositions of the present application are formulated as a pharmaceutical composition for use in a method of sedation, analgesia or treatment of anxiety or hypertension.

In certain non-limiting embodiments, the subject to be administered the ready to use dexmedetomidine composition is intubated. The subject may be intubated prior to, during or after administration of the dexmedetomidine composition. The subject may be intubated by the nasotracheal, endotracheal, direct oral laryngoscopy or by fiberoptic routes or via tracheotomy. As used herein an intensive care unit (ICU) refers to any setting that provides intensive care. The compositions of the application may be used for sedating a subject in an intensive care unit which means rendering a subject calm and treating conditions that affect subject comfort such as pain and anxiety in any setting that provides intensive care.

In other non-limiting examples, the ready to use compositions can be administered to a subject as a perioperative treatment. In certain embodiments, the compositions may be administered as a premedication to an operation. In certain embodiments, the ready to use compositions of the present application may be used in the manufacture of a medicament for perioperative treatment of mammals to reduce the responses of the autonomic nervous system to stressful stimuli during an operation.

In other non-limiting embodiments, the ready to use compositions may be administered to a patient as an adjunct anesthesia. For example, the composition may be administered with or without an amount of an anesthetic effective to achieve a desired level of local or general anesthesia. In certain embodiments, administration of the compositions of the present invention reduces the amount of anesthetic required to achieve a desired level of anesthesia.

In other non-limiting embodiments, the subject is critically ill. In one embodiment the subject suffers from one or more medical conditions. In certain embodiments the medical condition relates to the lungs, brain, heart, liver, kidney, eyes, ears, gastrointestinal system, or skin. Non-limiting examples may include, but are not limited to, respiratory distress syndrome, pneumonia, bronchopulmonary dysplasia, apnea of prematurity, pneumothorax, intraventricular hemorrhage, cerebral palsy, jaundice, patent ductus arteriosus, retinopathy of prematurity, myopia, strabismus, glaucoma, heroin withdrawal, alcohol fetal syndrome and Tay-Sachs disease.

In certain non-limiting embodiments, the ready to use dexmedetomidine compositions and solutions may be administered as a single continuous dose over a period of time. In other non-limiting examples the ready to used dexmedetomidine compositions and solutions may be administered as a loading dose followed by a maintenance dose over a period of time. In certain non-limiting examples, the dosage of the ready to use compositions and solutions is titrated until a desired effect is achieved.

In some subjects, the quality of the sedation achieved by administering the ready to use dexmedetomidine composition of the present application may be unique. In one non-limiting example, the subject may be arousable and oriented; the subject may be awakened and may respond to questions. In other non-limiting examples, an increased dose of a composition may be administered to transit the subject into a deeper level of sedation.

The Precedex® related substances method was developed to detect impurities at ppb levels. This method requires detection at non-discriminating low wavelength of 210 nm and high injection volume of 500 µl, which render it highly sensitive to detect any organic impurity, including stopper extractables. The presence, concentration and type of leachable may be analyzed using LC-MS. Potential leachable compounds may include, but are not limited to fenozan acid (chemical name 3-(3,5-di-tert-butyl-4-hydroxyphenyl-propionic acid, molecular weight 278.39 and CASRN 20170-32.5). Leachables may be present at levels lower than 540 µg/day, 500 µg/day, 450 µg/day, 400 µg/day, 350 µg/day, 300 µg/day, 250 µg/day, 200 µg/day, 150 µg/day, 100 µg/day, 50 µg/day, 45 µg/day, 40 µg/day, or 35 µg/day, depending upon the leachable of interest. It is recognized that different leachables may be present at different levels. Leachables may be analyzed by any method known in the art including, but not limited to, LC-MS and HPLC; leachable concentration may be reported as ppm, ppb, µg/day or any other standard known in the art. It is also recognized that different plastic vessels may yield different leachable profiles.

Dexmedetomidine solutions and liquid pharmaceutical compositions comprising dexmedetomidine solutions are known in the art to experience decrease of dexmedetomidine concentration during storage. The lack of stability during storage interferes with medical care and increases medical costs. The current application provides liquid pharmaceutical compositions comprising dexmedetomidine or a pharmaceutically acceptable salt thereof and ready to use sterile solutions comprising dexmedetomidine disposed or packaged within sealed plastic containers, wherein the concentration of dexmedetomidine remains relatively stable. In various non-limiting embodiments, the liquid pharmaceutical compositions or sterile dexmedetomidine solutions of the present application exhibit no more than a 5% decrease, no more than a 4% decrease, no more than a 3% decrease, no more than a 2% decrease, no more than a 1% decrease, no more than a 0.5% decrease or no more than a 0.1% decrease in the concentration of dexmedetomidine when the solutions are stored within a sealed plastic container for at least three months. In various non-limiting embodiments, the liquid pharmaceutical compositions or sterile dexmedetomidine solutions of the present application exhibit no more than a 5% decrease, no more than a 4% decrease, no more than a 3% decrease, no more than a 2% decrease, no more than a 1% decrease, no more than a 0.5% decrease or no more than a 0.1% decrease in the concentration of dexmedetomidine when the solutions are stored within a sealed plastic container for at least three, four, five, six, seven, eight, nine, ten, eleven, or twelve months.

Methods of providing dexmedetomidine to a subject in need thereof are provided. In various embodiments of the methods, a ready to use liquid pharmaceutical composition comprising dexmedetomidine or a pharmaceutically acceptable salt thereof and sodium chloride or a ready to use sterile dexmedetomidine solution disposed or packaged within a sealed plastic container is provided to a subject. The liquid pharmaceutical composition or solution may be administered to the subject by any method of administering compositions or solutions to a subject known in the art. Such methods of administering may include, but are not limited to, parenteral and oral administration methods.

The following examples are offered by way of illustration and not limitation.

EXPERIMENTAL

Example 1. Ready to Use Dexmedetomidine Injection Formulation

Premixed, ready to use dexmedetomidine compositions were developed in and packaged in RTU Technoflex PP Inerta™ bags of 50 ml and 100 ml size. Technoflex PP Inerta™ bags are multi-layered polypropylene bags manufactured by Technoflex (France). Technoflex Inerta™ over-wraps are manufactured by Technoflex (France). Formulation composition of the dexmedetomidine injection solutions are presented in Table 1.

TABLE 1

Formulation composition of Dexmedetomidine Injection premix formulation a) Dexmedetomidine Injection, 4 μg/mL-20mL fill

| Formulation Ingredient | Concentration (per mL) | % Amount/bag |
|---|---|---|
| Dexmedetomidine Hydrochloride, USP | 4 μg | 80 μg |
| Sodium Chloride, USP | 9 μg | 180 μg |
| Water for Injection, USP | QS to 1 mL | QS to 20 mL | b) Dexmedetomidine Injection, 4 μg/mL-50 mL fill

| Formulation Ingredient | Concentration (per mL) | % Amount/bag |
|---|---|---|
| Dexmedetomidine Hydrochloride, USP | 4 μg | 200 μg |
| Sodium Chloride, USP | 9 μg | 450 μg |
| Water for Injection, USP | QS to 1 mL | QS to 50 mL | c) Dexmedetomidine Injection, 4 μg/mL-100 mL fill

| Formulation Ingredient | Concentration (per mL) | % Amount/bag |
|---|---|---|
| Dexmedetomidine Hydrochloride, USP | 4 μg | 400 μg |
| Sodium Chloride, USP | 9 μg | 900 μg |
| Water for Injection, USP | QS to 1 mL | QS to 100 mL |

Multiple types of plastic container closure systems were evaluated for compatibility with the drug product. Results of the analysis for different bag systems are presented in Tables 2 and 3. T0 refers to beginning values. TS bags were terminally sterilized by moist heat sterilization. Non-TS bags were not subject to terminal sterilization procedures. Non-TS products were filtered by sterile grade filters. Significant decrease of the drug product Assay was noticed in both the plastic bags evaluated, indicating adsorption of dexmedetomidine in the indicated formulation for the tested bags.

TABLE 2

4 μg/mL Dexmedetomidine Injection premix formulation stability in EVA based DME bags

| Sample Description | pH | Assay (% LC) | Impurities (%) | Leachables (ppm) |
|---|---|---|---|---|
| Drug product bulk solution (Control) | 5.6 | 100.3 | <LOQ | 0.00 |
| Drug product in DME bag (EVA based), Non-TS, 7 day hold | 5.5 | 95.9 | <LOQ | 0.52 |

TABLE 3

4 μg/mL Dexmedetomidine Injection premix formulation stability in PVC-free DMP bags

| Sample Description | pH | Assay (% LC) | Impurities (%) | Leachables (ppm) |
|---|---|---|---|---|
| Drug product bulk solution (Control) | 5.2 | 93.8 | <LOQ | 0.03 |
| Drug product in DMP bag (PVC free), TS, 7 day hold | 5.2 | 87.8 | <LOQ | 0.07 |

*Assay of this batch is found to be lower than 100% LC. However, as the purpose of this experiment is to evaluate decrease of Assay in bag in comparison to control and the assay is still within drug product specifications, the data can still be used to make scientific decisions.

Container closure systems for dexmedetomidine pharmaceutical compositions or dexmedetomidine solutions in glass vials and plastic bags are described in Tables 4 and 5, respectively.

TABLE 4

Container closure system information for premixed Dexmedetomidine Injection, vial formulations Primary Packaging Materials Gerresheimer 20 mL GX-33 sulfur treated, clear, USP type I glass vial
Gerresheimer 50 mL GX-33 sulfur treated, clear, USP type I glass vial
Gerresheimer 100 mL sulfur treated, clear, USP type I glass vial with 28 mm closure
West 20 mm Novapure S10F451, 4432/50 coated stopper
Datwyler 28 mm Omniflex PLUS, FLCO coated stopper
Datwyler 20 mm flip-off seal
Datwyler 28 mm flip-off seal

TABLE 5

Container closure system information for premixed Dexmedetomidine Injection, Bag formulations Primary Packaging Materials Technoflex, Clear, Inerta Polypropylene, 50 mL bags
Technoflex, Clear, Inerta Polypropylene, 100 mL bags
Technoflex, Inerta Overwraps

Example 2. Dexmedetomidine Solution Stability Analysis

Dexmedetomidine injection formulations were prepared and disposed in 20 ml, 50 ml, 100 ml glass vials and 50 ml or 100 ml polypropylene bags with and without overwraps. Dexmedetomidine injection formulations in glass vials were placed on stability at 25° C.±2° C./60% RH±5% RH and 40° C.±2° C./75% RH±5% RH. Formulations in plastic bags were placed on stability at 25° C.±2° C./40% RH±5% RH, 30° C.±2° C./65% RH±5% RH and 40° C.±2° C./NMT 25% RH as per ICH guidelines. Drug product on stability was monitored for critical quality attributes including pH, Assay and Impurities at 3 months, 6 months, 9 months and 12 months. Storage at elevated temperature are commonly used in the industry to assess longer term chemical effects at non-accelerated conditions and to evaluate the effect of short term excursions outside the label storage conditions such as might occur during shipping. Results from studies of dexmedetomidine performed with temperature maintained at 40° C.±2° C./NMT 25% RH may be extrapolated to 24 months at room temperature. Stability at the elevated temperature indicates similar stability at room temperature at 24 months.

Results of pH analysis are presented in Table 6. T0 refers to beginning values. TS bags were terminally sterilized by moist heat sterilization. Non-TS bags were not subject to terminal sterilization procedures. Non-TS products were manufactured under aseptic conditions and sterilized by sterile filtration. pH levels of the solution in the polypropylene bags showed less variability than in the 20 ml glass vial. pH of the dexmedetomidine injection formulations in both glass vials and plastic bags were within drug product specifications throughout the study period.

TABLE 6

4 μg/mL Dexmedetomidine Injection premix formulation stability in vials and bags- pH analysis

| Sample Description | For Vials: 25° C. ± 2° C. 60% RH ± 5% For Bags: 25° C. ± 2° C. 40% RH ± 5% | | | | | 30° C. ± 2° C./ 65% RH ± 5% RH | | For Vials: 40° C. ± 2° C. 75% RH ± 5% For Bags: 40° C. ± 2° C. NMT 25% RH | |
|---|---|---|---|---|---|---|---|---|---|
| | T0 | 3 M | 6 M | 9 M | 12 M | 3 M | 6 M | 3 M | 6 M |
| Drug Product in 20 mL Vial-TS | 6.0 | 6.6 | 6.4 | N/A | N/A | 6.5 | 6.4 | 6.7 | 6.3 |
| Drug Product in 100 mL Vial-TS | 5.8 | 6.1 | 6.3 | N/A | N/A | 6.2 | 6.3 | 6.2 | 6.2 |
| Drug Product in 50 mL Bag-TS | 5.5 | 5.5 | 5.4 | N/A | 5.2 | 5.4 | 5.4 | 5.6 | 6.1 |
| Drug Product in 100 mL Bag- TS | 5.4 | 5.6 | 5.4 | 5.6 | 5.4 | 5.3 | 5.4 | 5.4 | 5.2 |
| Drug Product in 100 mL Bag- Non TS | 5.7 | 5.8 | 5.7 | 5.7 | 5.6 | N/A | N/A | 5.6 | 5.3 |
| Drug Product in 50 mL Bag with Overwrap-TS | 5.5 | 5.5 | 5.5 | N/A | N/A | 5.6 | 5.6 | 5.3 | 5.3 |
| Drug Product in 100 mL Bag with Overwrap- TS | 5.6 | 5.6 | 5.4 | N/A | N/A | 5.5 | 5.4 | 5.3 | 5.3 |

N/A- Samples not available

Results of the assay analysis are presented in Table 7. Assay of the drug product in glass vials as well as plastic bags under study is maintained within the specifications for accelerated stability conditions. Storage at elevated temperature are commonly used in the industry to assess longer term chemical effects at non-accelerated conditions and to evaluate the effect of short term excursions outside the label storage conditions such as might occur during shipping. Results from studies of dexmedetomidine performed with temperature maintained at 40° C.±2° C./NMT 25% RH may be extrapolated to 24 months at room temperature. Stability at the elevated temperature indicates similar stability at room temperature at 24 months. Assay of the drug product in plastic bags was also found to be within acceptable limits, indicating adsorption of dexmedetomidine is not a concern for the tested bags and the indicated formulation. We observed increase in assay values in bags without overwraps, specifically at 30° C.±2° C./65% RH±5% RH and 40° C.±2° C./NMT 25% RH. We believe this increase in assay is due to loss of solvent, water from the bag at higher temperature. The loss of water at higher temperature is controlled by adding bag overwraps which resulted in stable assay values at 30° C.±2° C./65% RH±5% RH and 40° C.±2° C./NMT 25% RH.

TABLE 7

4 μg/mL Dexmedetomidine Injection premix formulation stability in vials and bags- Assay analysis (% Label Claim)

| Sample Description | For Vials: 25° C. ± 2° C. 60% RH ± 5% For Bags: 25° C. ± 2° C. 40% RH ± 5% | | | | | 30° C. ± 2° C./ 65% RH ± 5% RH | | For Vials: 40° C. ± 2° C. 75% RH ± 5% For Bags: 40° C. ± 2° C. NMT 25% RH | |
|---|---|---|---|---|---|---|---|---|---|
| | T0 | 3 M | 6 M | 9 M | 12 M | 3 M | 6 M | 3 M | 6 M |
| Drug Product in 20 mL Vial | 100.3 | 98.1 | 98.6 | N/A | N/A | 98.2 | 98.5 | 97.8 | 97.7 |
| Drug Product in 100 mL Vial | 100.5 | 98.1 | 98.9 | N/A | N/A | 97.8 | 98.5 | 97.3 | 97.1 |
| Drug Product in 50 mL Bag | 99.0 | 99.6 | 100.5 | N/A | 99.0 | 100.1 | 100.2 | 105.2 | 111.7 |
| Drug Product in 100 mL Bag- TS | 99.2 | 99.1 | 99.9 | 99.3 | 99.2 | 99.3 | 99.2 | 102.4 | 106.6 |
| Drug Product in 100 mL Bag- Non TS | 100.8 | 101.1 | 101.7 | 101.4 | 100.8 | N/A | N/A | 104.6 | 108.9 |
| Drug Product in 50 mL Bag with Overwrap-TS | 96.9 | 96.1 | 96.5 | N/A | N/A | 96.5 | 96.7 | 95.0 | 94.3 |
| Drug Product in 100 mL Bag with Overwrap- TS | 98.3 | 97.2 | 97.3 | N/A | N/A | 96.4 | 97.5 | 96.6 | 96.4 |

N/A- Samples not available

Example 3. Drug Product Impurity Profile Analysis

Results of the drug product related impurity analysis are presented in Table 8. The impurities of the drug product in glass vials as well as plastic bags under study are maintained below limit of Quantification (LOQ) even for accelerated stability conditions.

the following conditions: 25° C.±2° C./40% RH±5% RH; 30° C.±2° C./65% RH±5% RH; or 40° C.±2° C./NMT 25% RH. Samples maintained under 25° C.±2° C./40% RH±5% RH or 30° C.±2° C./65% RH±5% RH conditions were stored for 1 month, 3 months, 6 months, 9 months or 12 months. Samples maintained at 40° C.±2° C./NMT 25% RH conditions were stored for 1, 3 or 6 months.

TABLE 8

4 µg/mL Dexmedetomidine Injection premix formulation stability in vials and bags- drug product impurity analysis (% Label Claim)

| Sample Description | For Vials: 25° C. ± 2° C. 60% RH ± 5% For Bags: 25° C. ± 2° C. 40% RH ± 5% | | | | | 30° C. ± 2° C./ 65% RH ± 5% RH | | For Vials: 40° C. ± 2° C. 75% RH ± 5% For Bags: 40° C. ± 2° C. NMT 25% RH | |
|---|---|---|---|---|---|---|---|---|---|
| | T0 | 3 M | 6 M | 9 M | 12 M | 3 M | 6 M | 3 M | 6 M |
| Drug Product in 20 mL Vial | <LOQ | <LOQ | <LOQ | N/A | N/A | <LOQ | <LOQ | <LOQ | <LOQ |
| Drug Product in 100 mL Vial | <LOQ | <LOQ | <LOQ | N/A | N/A | <LOQ | <LOQ | <LOQ | <LOQ |
| Drug Product in 50 mL Bag | <LOQ | <LOQ | <LOQ | N/A | <LOQ | <LOQ | <LOQ | <LOQ | <LOQ |
| Drug Product in 100 mL Bag- TS | <LOQ | <LOQ | <LOQ | <LOQ | <LOQ | <LOQ | <LOQ | <LOQ | <LOQ |
| Drug Product in 100 mL Bag- Non TS | <LOQ | <LOQ | <LOQ | <LOQ | <LOQ | <LOQ | <LOQ | <LOQ | <LOQ |
| Drug Product in 50 mL Bag with Overwrap-TS | <LOQ | <LOQ | <LOQ | N/A | N/A | <LOQ | <LOQ | <LOQ | 0.44* |
| Drug Product in 100 mL Bag with Overwrap- TS | <LOQ | <LOQ | <LOQ | N/A | N/A | <LOQ | <LOQ | <LOQ | 0.29* |

N/A- Samples not available
*Impurities observed are lower than Identification threshold (0.5%) and Qualification threshold (1.0%) for the drug product Dexmedetomidine Bag v Placebo Bag Leachable Profile Analysis On terminal sterilization by moist heat sterilization, plastic Inerta® polypropylene bags are known to leach few compounds. These leachables were observed in both Dexmedetomidine solution containing bags as well as placebo containing bags. The leachables were evaluated for toxicological risk assessment and found to be below allowable daily exposure.

Example 4. Effect of N₂ Purge on Dexmedetomidine HCL 4 µg/ml Solution Stability

Dexmedetomidine-HCl (4 µg/ml) sodium chloride solutions were prepared with or without sparging with N₂ for 20 minutes and filled in 20 mL Gerresheimer GX-33 sulfur treated, clear, USP type I glass vials. Samples were placed on stability at 25° C.±2° C./60% RH±5% RH, 30° C.±2° C./65% RH±5% RH, and 40° C.±2° C./75% RH±5% RH and evaluated at pre-determined time points (1 month, 3 months and 6 months) for critical quality attributes.

Example 5. Dexmedetomidine HCl Injection Accelerated and Long Term Stability Study Dexmedetomidine-HCl Injection (4 µg/ml) solutions were prepared and filled in 50 ml and 100 mL Technoflex Inerta® polypropylene (PP) bags. Placebo solutions of the injection (0.9% sodium chloride) were also prepared and filled in polypropylene bags. Samples were stored horizontally under Example 6. Leachable Analysis Dexmedetomidine Injection 4 µg/ml and 0.9% sodium chloride solutions were prepared and filled into Technoflex Inerta® polypropylene (PP) bags. Multiple types of plastic container closure systems were evaluated. To serve as control, placebo solutions of the injection (0.9% sodium chloride) were also prepared and filled in polypropylene bags. In addition, Dexmedetomidine Injection 4 µg/ml solutions were also filled into glass vials. Plastic samples were placed on stability at 25° C.±2° C./40% RH±5% RH; 30° C.±2° C./65% RH±5% RH; and 40° C.±2° C./NMT 25% RH. Glass samples were placed on stability at 25° C.±2° C./60% RH±5% RH, and 40° C.±2° C./75% RH±5% RH. At various time points, these samples were monitored for unknown peaks on HPLC (High Pressure Liquid Chromatography) to analyze leachables.

Although the foregoing invention has been described in some detail by way of illustration and example for purposes of clarity of understanding, it will be obvious that certain changes and modifications may be practiced within the scope of the claims.

We claim:

1. A ready to use liquid pharmaceutical composition for parenteral administration to a subject, comprising dexmedetomidine or a pharmaceutically acceptable salt thereof and sodium chloride in an aqueous solution disposed within a sealed plastic container, wherein said liquid pharmaceutical composition when stored in said plastic container for six months at 40° C.±2° C./NMT 25% RH, exhibits no more than a 5% decrease in the concentration of dexmedetomidine.

2. The ready to use liquid pharmaceutical composition of claim 1, wherein said plastic container is a rigid plastic container, bag, sack, tube, ampule, vial or syringe.

3. The ready to use liquid pharmaceutical composition of claim 1, wherein said dexmedetomidine or pharmaceutically acceptable salt thereof is at a concentration of about 0.005 to about 100 μg/ml.

4. The ready to use liquid pharmaceutical composition of claim 3, wherein said dexmedetomidine or pharmaceutically acceptable salt thereof is at a concentration of about 0.5 to about 10 μg/ml.

5. The ready to use liquid pharmaceutical composition of claim 1, wherein said sodium chloride is at a concentration of between about 1 to about 20.0 mg/ml.

6. The ready to use liquid pharmaceutical composition of claim 5, wherein said sodium chloride is at a concentration of between about 7 to about 12 mg/ml.

7. The ready to use liquid pharmaceutical composition of claim 1, wherein said liquid pharmaceutical composition when stored in the plastic container exhibits no more than a 5% decrease in the concentration of dexmedetomidine.

8. The ready to use liquid pharmaceutical composition of claim 1, wherein said liquid pharmaceutical composition when stored in the plastic container exhibits no more than a 2% decrease in the concentration of dexmedetomidine.

9. The ready to use liquid pharmaceutical composition of claim 1, wherein said liquid pharmaceutical composition when stored in the plastic container exhibits no more than a 1% decrease in the concentration of dexmedetomidine.

10. The ready to use liquid pharmaceutical composition of claim 1, wherein said liquid pharmaceutical composition when stored in the plastic container for six months exhibits no more than a 0.5% decrease in the concentration of dexmedetomidine.

11. The ready to use liquid pharmaceutical composition of claim 1, wherein said liquid pharmaceutical composition is formulated as a total volume selected from the group consisting of 20 ml, 50 ml and 100 ml.

12. The ready to use liquid pharmaceutical composition of claim 2, wherein said plastic container is a bag with or without an overwrap.

13. A premixed, ready to use sterile dexmedetomidine solution consisting of dexmedetomidine and sodium chloride in an aqueous solution packaged in a sealed plastic container, wherein the dexmedetomidine solution when stored in said plastic container for six months at 40° C.±2° C./NMT 25% RH exhibits no more than 2% decrease in the concentration of dexmedetomidine.

14. The dexmedetomidine solution of claim 13, wherein said plastic container is a rigid plastic container, bag, sack, tube, ampule, vial or syringe.

15. The dexmedetomidine solution of claim 13, wherein said dexmedetomidine or pharmaceutically acceptable salt thereof is at a concentration of about 0.005 to about 100 μg/ml.

16. The dexmedetomidine solution of claim 13, wherein said sodium chloride is at a concentration of between about 1 to about 20.0 mg/ml.

17. The dexmedetomidine solution of claim 13, wherein said plastic container is a bag with or without an overwrap.

18. The dexmedetomidine solution of claim 13, wherein the dexmedetomidine solution is administered perioperatively.

19. The dexmedetomidine solution of claim 13, wherein the dexmedetomidine solution is administered before or after surgery.

20. The dexmedetomidine solution of claim 13, wherein the dexmedetomidine solution is administered as an analgesic, an anxiolytic, an adjunct to anesthesia, a sedative, or an anti-hypertensive agent.

* * * * *